(12) United States Patent
Akiyama (10) Patent No.: US 7,221,443 B2
(45) Date of Patent: May 22, 2007

(54) APPEARANCE INSPECTION APPARATUS AND METHOD OF IMAGE CAPTURING USING THE SAME

(75) Inventor: Yoshihiro Akiyama, Kanagawa-ken (JP)

(73) Assignee: SAKI Corporation (JP)

( * ) Notice: Subject to any disclaimer, the term of this patent is extended or adjusted under 35 U.S.C. 154(b) by 297 days.

(21) Appl. No.: 10/764,098

(22) Filed: Jan. 23, 2004

(65) Prior Publication Data

US 2004/0218040 A1 Nov. 4, 2004

(30) Foreign Application Priority Data

Jan. 24, 2003 (JP) ............... 2003-016475

(51) Int. Cl.
*G01N 21/00* (2006.01)
*G02B 27/10* (2006.01)

(52) U.S. Cl. ............... 356/237.1; 356/237.3; 359/619

(58) Field of Classification Search .. 356/237.1–237.6, 356/394; 382/167, 162, 135, 318; 359/619; 358/451, 453
See application file for complete search history.

(56) References Cited

U.S. PATENT DOCUMENTS

| 4,947,666 | A | * | 8/1990 | Hametner et al. ............ 72/37 |
|---|---|---|---|---|
| 4,978,224 | A | * | 12/1990 | Kishimoto et al. ......... 356/394 |
| 5,130,820 | A | * | 7/1992 | Hirota ........................ 358/447 |
| 5,191,441 | A | * | 3/1993 | Suzuki et al. ............... 358/451 |
| 5,197,105 | A | * | 3/1993 | Uemura et al. ............. 382/147 |
| 5,880,828 | A | * | 3/1999 | Nakamura et al. ....... 356/237.3 |
| 5,880,859 | A | * | 3/1999 | Hiromatsu .................. 358/514 |
| 6,424,735 | B1 | * | 7/2002 | Freifeld ...................... 382/154 |
| 6,437,312 | B1 | * | 8/2002 | Adler et al. ................. 250/216 |
| 6,552,783 | B1 | * | 4/2003 | Schmidt et al. .......... 356/237.4 |
| 6,560,024 | B2 | | 5/2003 | Akiyama et al. |
| 6,678,402 | B2 | * | 1/2004 | Jones et al. ................. 382/135 |
| 7,002,676 | B2 | * | 2/2006 | Akiyama ................. 356/237.2 |
| 2003/0031362 | A1 | * | 2/2003 | Keithley ..................... 382/167 |

FOREIGN PATENT DOCUMENTS

JP     09113361 A   *   5/1997

* cited by examiner

*Primary Examiner*—Sang H. Nguyen
(74) *Attorney, Agent, or Firm*—Anderson Kill & Olick, PC

(57) ABSTRACT

The present invention is an appearance inspection apparatus and method utilizing multiple light sources in a lighting unit 30 to alternately irradiate, line by line, side light from a side light source and slit light from a slit light source onto board 1 to be inspected. A correction value memory unit stores digital correction values required for correcting shadings for the side light source and the slit light source and an analysis unit utilizes these digital correction values to correct shadings on the image data. A highly accurate image is thus obtained.

4 Claims, 10 Drawing Sheets

APPEARANCE INSPECTION APPARATUS AND METHOD OF IMAGE CAPTURING USING THE SAME

FIELD OF THE INVENTION

The present invention relates to a technology for inspecting the appearance of a body such as an electronic circuit board to detect defects. More specifically, the present invention relates to a technology that provides an accurate image of the appearance of a body for inspection of defects.

BACKGROUND OF THE INVENTION

IC chips or LSI chips are typically bonded onto a circuit board by soldering. The soldering steps comprise: application of a cream type solder (hereinafter referred to as "soldering cream") onto electrodes mounted in the board using a screen printing machine; coating the lead wires of the chips with soldering cream and heating the cream type solder using a reflowing machine e.g. an oven. Insufficient application of soldering cream may cause the soldering to fail. It is therefore important that the coating state of the cream solder be inspected before the chips are mounted onto the board. In the case of BGAs (Ball Grid Arrays), an input pad and an output pad are arranged on the back of the package. Once the BGA chips are bonded onto the board, inspection of soldering conditions are too late. Soldering conditions must be inspected before the BGA chips are bonded onto the board.

To accurately detect defects, the inspection apparatus for inspecting the soldering cream coating conditions must provide a very high resolution of the captured image of the board with a resolution corresponding to the packaging density. Moreover, due to time constraints in the packaging process, the inspection operation must be conducted quickly and without causing a delay in shipment. It should be noted that one bad product found in a shipment generates additional jobs such as collection, repair, re-shipment that would not have been required otherwise. Profits from sales may not cover the cost of all these additional jobs.

Conventional inspection apparatus inspects the soldering cream coating condition on the body to be inspected by measuring the area within which a soldering cream is coated. Since it is essential for an appropriate amount of soldering cream to be coated onto a chip to effectuate normal soldering, the appropriate amount and not the coating area should be measured to perform an accurate inspection. Without a highly accurate volume measurement of the soldering cream, there is no accurate inspection. Accordingly, to perform a highly accurate inspection, the volume measurement of the soldering cream is essential.

An apparatus which irradiates a line pattern onto a board through a slit in a light projector with the image of the board captured using a camera to analyze the shape of the soldering paste is taught in Japanese unexamined patent (Kokai) No. H05-187838.

PROBLEMS TO BE SOLVED

The apparatus disclosed in the aforementioned patent publication moves the board along the X- and Y-directions to irradiate light from slitted openings onto a solder paste in a specific area and inspects the captured image from the irradiated light at a 20–30 μm pixel pitch utilizing a charged-coupled device (CCD) having 1 million pixels within a range of 2–3 cm on each side at one time. Using this approach, inspection of the entire board takes too long. A mother board for use in laptop computers, for example, has 2,000–4,000 solder print points. An appearance inspection apparatus in which image capturing points along the X- or Y-direction are inspected limited to only 100–200 points is inadequate. This is because production lines must inspect a mother board within 30 seconds, which means that an all-point inspection takes too long and leads to poor production management as well.

Users desire an appearance inspection apparatus that provides a clear image in which one can discriminate the board's soldering condition at a glance. An appearance image with inconsistent contrast adversely affects accuracy and the reliability of the appearance inspection.

SUMMARY OF THE INVENTION

The appearance inspection apparatus of the present invention comprises: a scanning head for scanning the body to be inspected; and a main unit for controlling the apparatus and scanning head with the scanning head further comprising: a lighting unit having multiple light sources for projecting light onto the surface of the body to be inspected; and at least one one-dimensional sensor having at least a plurality of arrays of multiple image capturing elements for detecting reflected light from the inspection surface in a vertically upward direction to produce image data. The main unit further comprises: a head control unit, which switches the multiple light sources in the lighting unit into different lighting states and controls relative motion of the scanning head relative to the body to be inspected; a memory head control unit for storing in memory image data produced by the one-dimensional sensor; and an analysis unit for correcting shading of the image data in accordance with different lighting states switched by the head control unit to obtain an appearance inspection image of the body to be inspected. According to the appearance inspection apparatus, uneven sensitivity of the one-dimensional sensor or uneven luminous energy of light sources can be corrected through calibration of shading in the obtained image data for each light source obtained by switching.

In accordance with the description of the present invention, "scanning" means that the scanning head's motion is perpendicular to the direction in which the image capturing elements of the one-dimensional sensor are arranged. Moreover, the direction of the scanning head's motion is referred to as the "moving direction" and the relative motion between the scanning head and a body to be inspected is referred to as the "scanning direction". Detection of a reflected light for one line is called "image capturing" to differentiate this image detection from scanning. An array of multiple elements may be arranged at a given pitch. Reflected light that is reflected vertically upward from the inspection surface may be reflected light at a "0" outgoing angle.

It is desirable that the one-dimensional sensor comprises a plurality of arrays of multiple RGB (red, green, and blue) image capturing elements. It is also desirable that the main unit further comprises a correction value memory unit in which a digital correction value is stored as a table for each of the RGB image capturing elements wherein the correction value is utilized to correct shading corresponding to a specific lighting state generated by switching the light source. It is further desirable that the analysis unit corrects shading for the image data with reference to the table kept in the correction value memory unit. The multiple light sources in the scanning head may further comprise: a side light source, which projects light onto the surface of the body to be inspected at an angle; a slit light source, which projects a slit light at an angle. The head control unit may alternately switch the side light source and the slit light source for lighting.

The method of the present invention is a method for obtaining an image of an object comprising switching multiple light sources onto the object to project light to produce image data from the light reflected from the object and correcting the shading of the image data based on a correction value that corresponds to a specific lighting state provided by switching the multiple light sources. This method provides an appropriate shading correction to image data in accordance with the lighting state, thereby providing a clear image of the object.

BRIEF DESCRIPTION OF THE DRAWINGS

FIGS. 7[(a) and (b)] are diagrams illustrating the stripe pattern formed by irradiating slit light onto a board having cream coatings of solder.

DETAILED DESCRIPTION OF PREFERRED EMBODIMENTS

Figure 1:
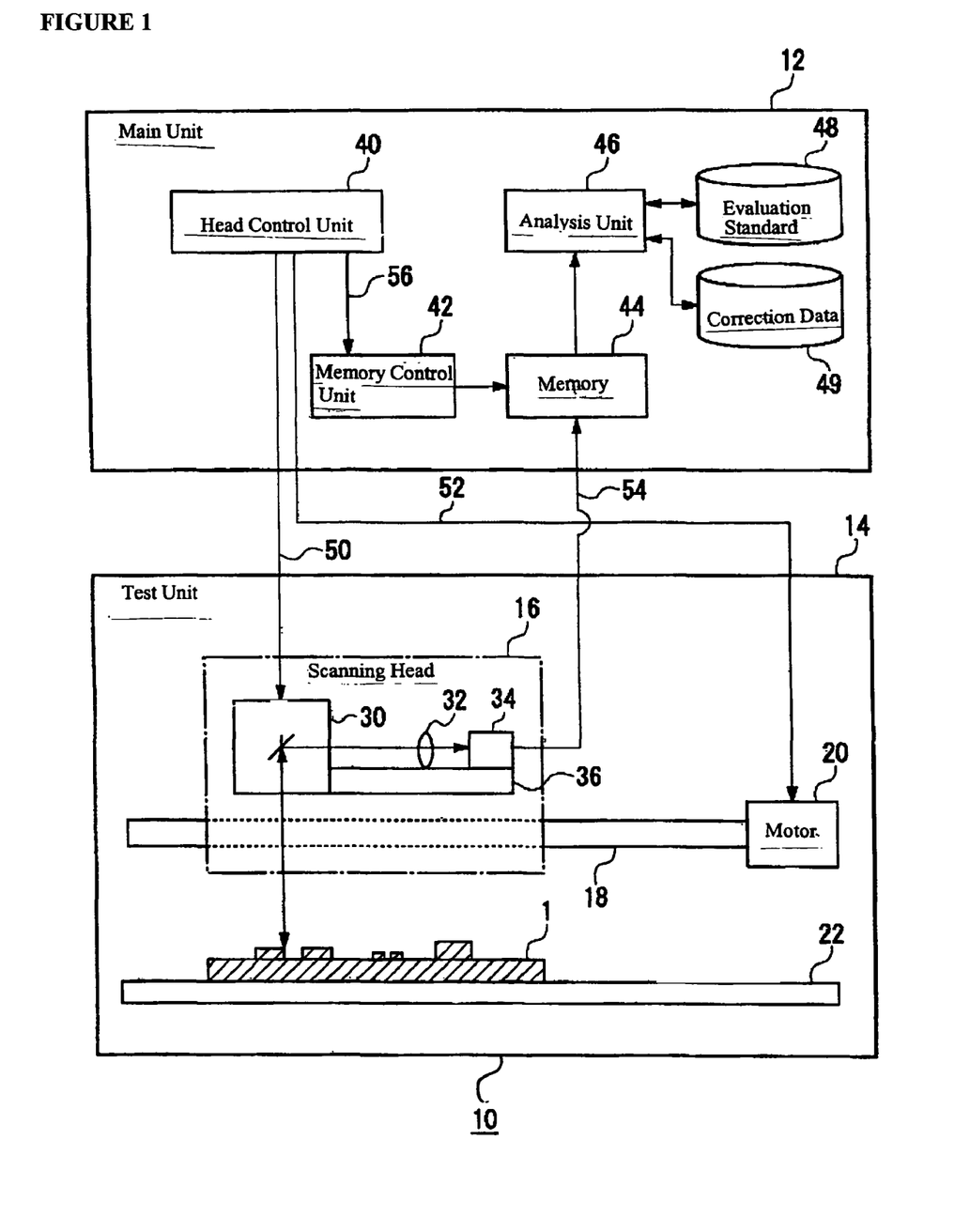
FIG. 1 illustrates the overall configuration of the appearance inspection apparatus associated with Embodiment 1.

FIG. 1 illustrates a configuration of the appearance inspection apparatus 10 of the present invention inclusive of a main unit 12 and a test unit 14. This apparatus creates a color image by scanning the surface of a body to be inspected using a line sensor to check the coating state of the soldering cream through image discrimination. A line-by-line image is obtained by moving a scanning head perpendicular to the direction of the array of image capturing elements in the line sensor, followed by a one-dimensional motion of the scanning head for inspection to be completed by passing or failing the inspected body.

As illustrated in FIG. 1, the test unit 14 includes a support base 22 upon which a circuit board 1 is mounted. The circuit board is the body to be inspected. A scanning head 16, a stepping motor 20 which moves the scanning head 16, and a guide 18 (e.g. linear guide) for holding scanning head 16 are supported above the support base 22.

The scanning head 16 has a lighting unit 30, a lens 32 and a line sensor 34. These members are secured onto a common frame 36. The lighting unit 30, as will be described in more detail hereafter, includes a side light source, a slit light source and a half mirror. Reflected light that is reflected vertically upward from board 1 is guided to pass through lens 32 via a half mirror, and is input to line sensor 34, which is a one dimensional CCD sensor. Line sensor 34 captures the image of board 1 line by line as output image data 54. Line sensor 34 includes an array of multiple image capturing elements each corresponding to three (RGB) colors separated by a color filter.

Main unit 12 controls the apparatus and includes a CPU, memory, or LSI of any computer; software thereof may be a program having an appearance inspection function loaded onto a memory. In FIG. 1 the functional blocks are actualized by interaction between hardware and software. It is apparent to one of ordinary skill in the art that the functional block may be actualized by hardware only or software only, or a combination of hardware and software.

Figure 2:
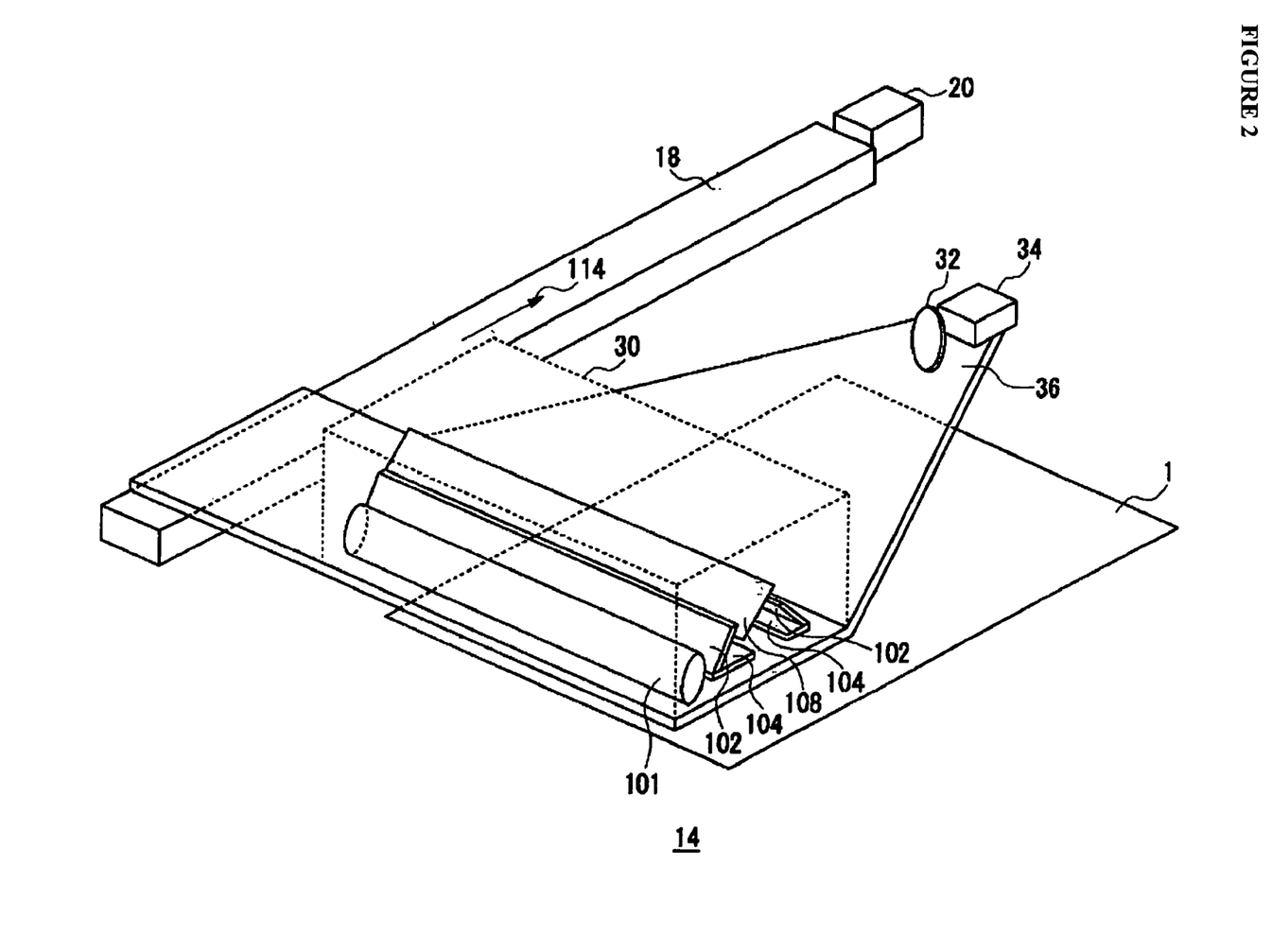
FIG. 2 is a perspective view of the test unit of FIG. 1.

Head control unit 40 of main unit 12 first supplies a lighting control clock signal 50 to lighting unit 30 which lights up alternately the vertical lighting and side lighting for each line. Therefore, lighting unit 30 produces two lighting states including a first side lighting state from the side lighting source 102 and a second slit lighting state from the slit light source 103 (FIG. 2). Head control unit 40 further outputs motor control signal 52 to motor 20 and test start signal 56 to memory control unit 42. Motor control signal 52 controls the stepping of motor 20 which is a step motor. Motor 20 moves scanning head 16 to one edge of board 1 when inspection begins representing the initial position. Scanning head 16 captures the image of one line of image data 54 every time it moves by one line. The image data 54 is three color (RGB) image data obtained every time an image of one line is captured. Also, memory control unit 42 controls writing of image data 54 with reference to the test-start signal 56. Afterwards, image data 54 is recorded in memory 44 for storage line by line. Each line of image data 54 comprises data from the side lighting source obtained under the vertical lighting; and data obtained under the slit light source in a selective manner. As images of all lines are captured, one appearance inspection image captured by the vertical lighting and the other appearance inspection image captured by the slit lighting are separately stored in memory 44. The appearance inspection image is a synthesized RGB data image data which may be a synthesized three RGB color data image derived from the height measurement image. Note that the configuration in memory 44, and the arrangement of image data 54 therein has some degree of freedom in memory design, therefore, a variety of configurations are possible. For example, two independent memory regions may be provided in memory 44 such that the appearance inspection image and the height measurement image can be stored separately; memory control unit 42 may be controlled in such a manner that line by line image data 54 is separately stored in different memory regions. Alternately, the appearance inspection image and the height measurement image may be stored in a single memory region in memory 44 and memory control unit 42 may break down the image data 54 on a line by line basis to interleave each line for storage.

Analysis unit 46 reads out, during or after the completion of scanning, the appearance inspection image data and the height measurement image data from memory 44. Correction value memory unit 49 retains a digital correction value of each RGB image capturing element of line sensor 34 in the form of a table for each lighting state such that the digital correction value may be used for correcting shading of image data corresponding to each lighting state of lighting unit 30. In other words, correction value memory unit 49 has tables illustrating digital correction values for each lighting type, such as those obtained under lighting state (1) the side lighting; and those obtained under lighting state (2) the slit lighting. The digital correction values are set up for each of the multiple light sources that are present in lighting unit 30, in such a manner that an uneven lens 32, uneven sensitivities of the line sensor 34, and uneven luminous energy of each light source are corrected or offset. When multiple light sources are combined to light up simultaneously in lighting unit 30, a digital correction value for the combination is also set up.

Analysis unit 46 corrects shading for image data of an appearance inspection image and a height measurement image with reference to the table retained in correction value memory unit 49. More specifically, a table that is set up for side lighting is referenced for the appearance inspection image data; another table that is set up for slit lighting is referenced for the height measurement image data. These tables allow analysis unit 46 to obtain a clear appearance inspection image and a height measurement image that are free from uneven contrast. Analysis unit 46 also provides for pass or failure checking of the coating state of a soldering cream appearing in the resulting appearance inspection image and also the resulting height measurement image with reference to the evaluation standard recorded in evaluation standard memory unit 48 in advance. Finally, validity of soldering points on which soldering cream is coated is checked with reference to the appearance inspection image, followed by measurement of the area in which the soldering cream is coated. Then, the height of the coated soldering cream is measured with reference to the height measurement image, followed by measurement of the area defined by soldering cream coating. The volume of the soldering cream is further calculated utilizing the area previously measured to check whether the amount of coating is appropriate.

Figure 3:
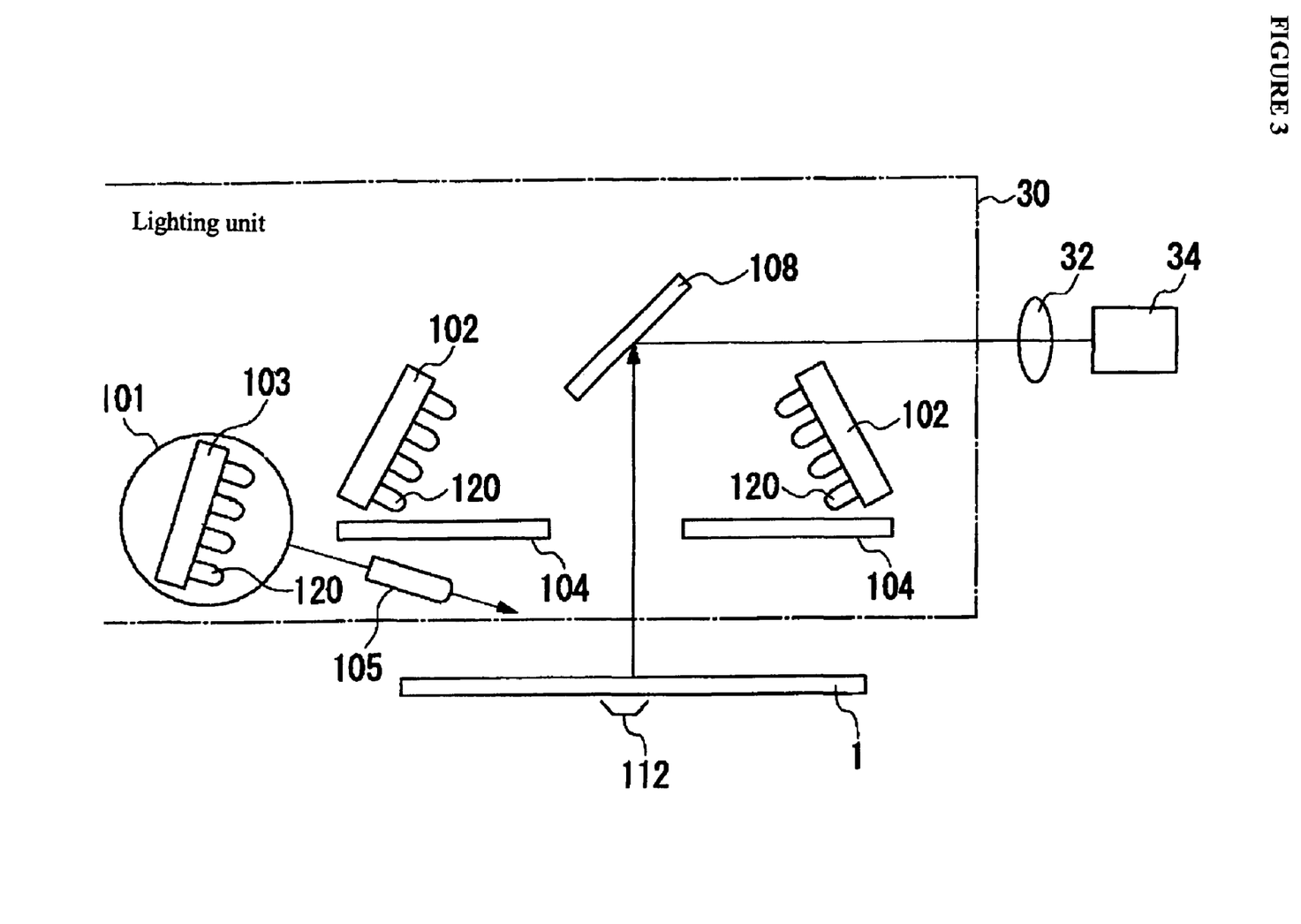
FIG. 3 is a configuration of a scanning unit including a lighting unit.

FIG. 2 is a perspective view of the test unit 14 with FIG. 3 illustrating the configuration of the lighting unit 30 from an initial starting point. When an image data for one line is captured in the state illustrated in FIG. 2 or 3, scanning head 16 moves one line in the moving direction 114 by guide 18. By repeating the same steps, the overall image data of board 1 is obtained.

Figure 9:
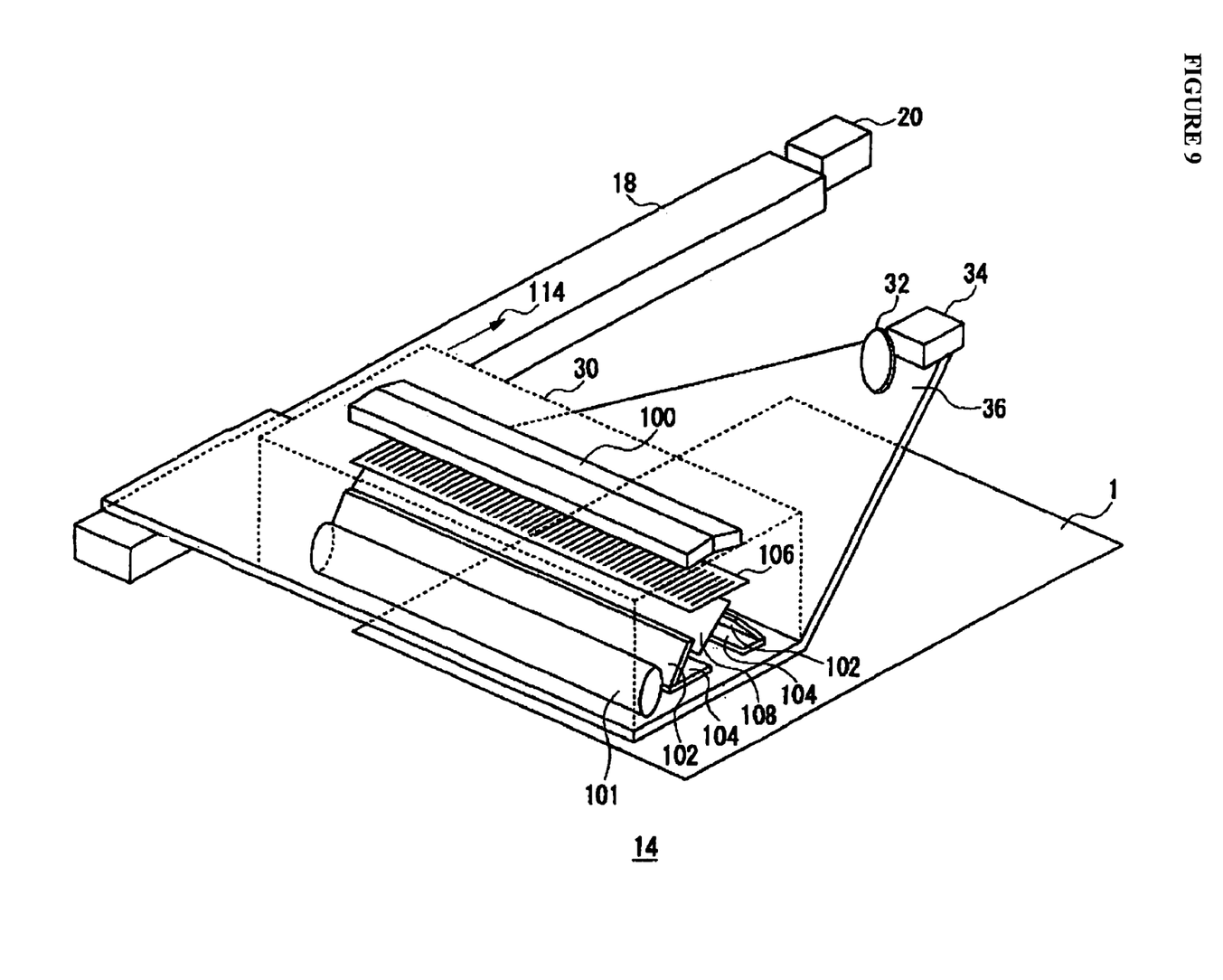
FIG. 9 is a perspective view of the test unit associated with Embodiment 2.

An acrylic sheet 104 is provided under the side light source 102 of lighting unit 30 and the slit light source 103 is included within a rotary cylinder 101, which is cylindrical in configuration. Multiple parallel slits (not shown) are provided on the outer circumference of rotary cylinder 101 such that light emitted from the light source 103 passes these slits to become slit light (FIG. 9). The slit light forms a stripe pattern (FIG. 5) on the inspection surface. The lighting unit 30 may include multiple light sources.

As illustrated in FIG. 3, two side light sources 102, each having LEDs (light emitting diodes) inclined at an angle such that they project side light onto the line 112 under inspection. Acrylic sheet 104 diffuses the side light projected from the side light source 102. Side light source 102 comprises an array of LEDs 120 each of which are spot light sources. Without diffusion, the spot light from each LED is superimposed onto image data, adversely affecting inspection accuracy.

Slit light source 103 also has an array of LEDs 120 as its light source and produces a slit light through a slit mask pattern formed by multiple slits (not shown) provided on the outer circumference of rotary cylinder 101 (not shown). The slit light is then converged by a short-focus imaging element array 105 and is projected as a pattern of stripes (FIG. 5) onto line 112 on the inspection surface of board 1. The catoptrical light from line 112 is further reflected onto half mirror 108 and redirected into line sensor 34 via lens 32.

Utilizing a commercially available "SELFOC" LENS ARRAY for the short-focus imaging element array 105, a stripe pattern may be projected as a line within a small space. The torque generated by rotary cylinder 101 can be controlled together with the movement of scanning head 16 at the same time such that any rotation ensures a continual stripe pattern and narrows the stripe-to-stripe interval, thereby enhancing the height measurement resolution.

Figure 4:
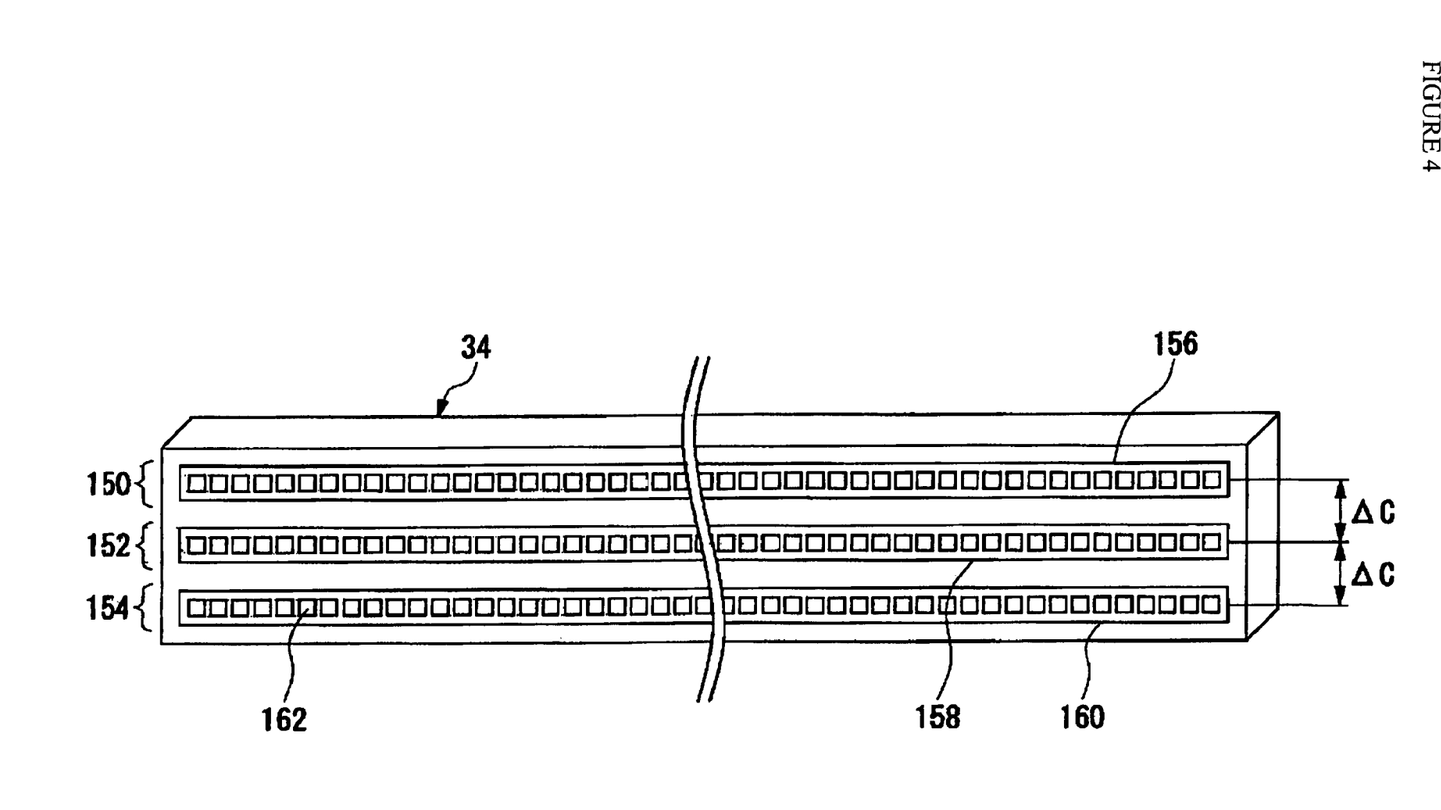
FIG. 4 is a configuration of a line sensor.

FIG. 4 is a configuration of the line sensor 34. Line sensor 34 comprises: an array of red image capturing elements 150; an array of green image capturing elements 152; and an array of blue image capturing elements 154; with each array corresponding to the three colors red, green, and blue (RGB) respectively. Each of the line sensor arrays has 5,000–10,000 image capturing elements 162. The array of red image capturing elements 150 has a red color filter 156 at the incident surface to extract the red component. In a similar manner, the array of green image capturing elements 152 has a green color filter 158 that extracts the green component and the array of blue image capturing elements 154 has a blue color filter 160 that extracts the blue components with each of the arrays provided at the incident surface thereof. The pitch between the red image capturing element array 150, and the green image capturing element array 152, and the pitch between the green image capturing element array 152 and the blue image capturing element array 154 is kept at $\Delta C$ which is substantially equal in size.

Figure 5:
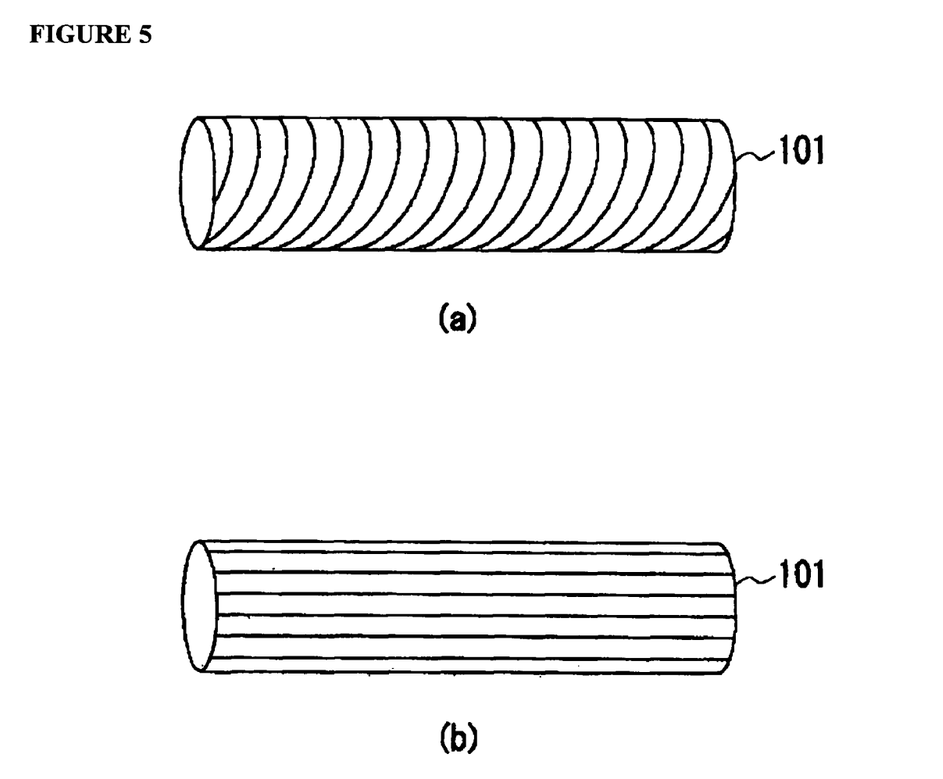
FIG. 5 is a diagram illustrating a slit mask pattern of a rotary cylinder used for a slit light source.

FIGS. 5(*a*) and (*b*) are diagrams illustrating slit mask patterns provided on the surface of rotary cylinder 101. LC chips or LSI chips are usually arranged in parallel with the vertical or horizontal direction of board 1, and rarely arranged at an angle. For this reason, it is desirable that the stripe pattern of slit light is formed at 45 degrees to the coating area of the soldering cream to obtain enough stripe patterns generated onto the area coated with solder regardless of the fact that a chip is arranged in the vertical or horizontal direction. In FIG. 5(*a*), a slit mask pattern is formed on the surface of rotary cylinder 101 at 45 degrees. The slit mask pattern may be formed in such a manner that the stripe pattern is generated in parallel with the direction in which image capturing elements of line sensor 34 are arranged.

Figure 6:
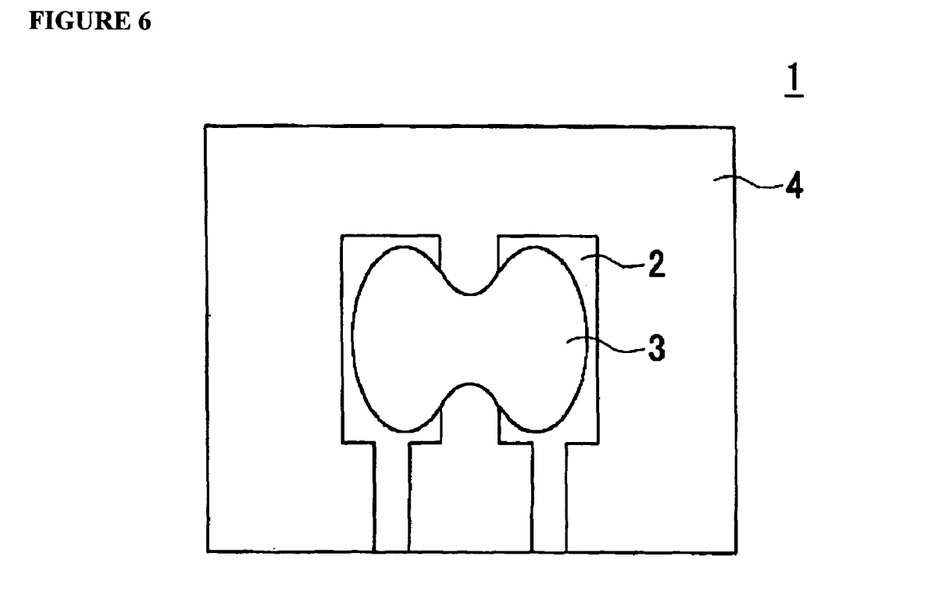
FIG. 6 is a diagram illustrating a board on which a soldering cream is coated.

FIG. 6 is a diagram illustrating board 1 on which a soldering cream is coated. Electrode 2 is coated with soldering cream 3. Components other than electrode 2 on board 1 are coated with semitransparent solder resist film 4. Therefore the soldering cream 3 applied on top of solder resist film 4 will melt away as a result of reflowing.

Figure 7:
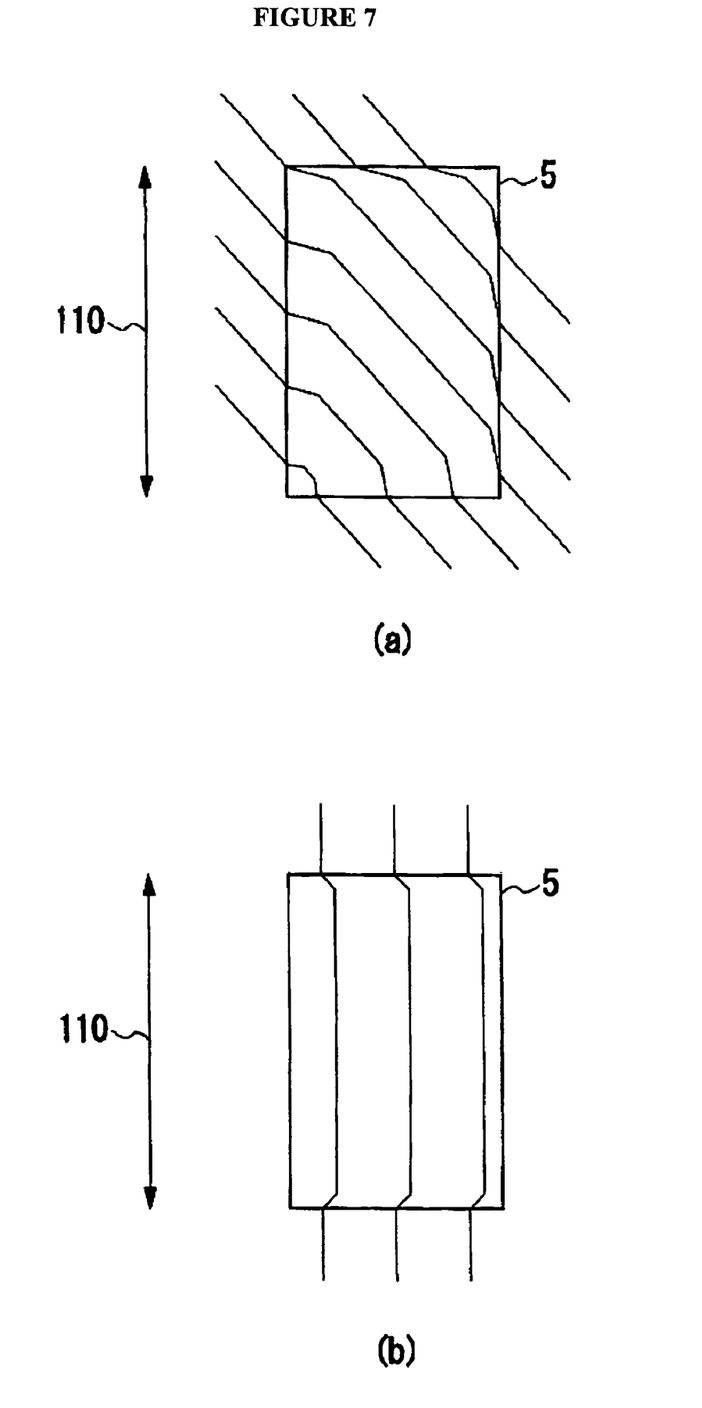

FIGS. 7(*a*) and (*b*) are diagrams illustrating the stripe pattern formed by irradiating slit light onto board 1 having soldering cream coatings. FIGS. 7(*a*) and (*b*) are stripe patterns formed by slit light irradiated on board 1 utilizing the slit mask patterns illustrated in FIGS. 5(*a*) and (*b*).

The long side of the solder coated area 5 as shown in FIG. 7(*b*) lies in parallel with the arrangement direction 110 of image capturing elements of line sensor 34. The use of a slit mask pattern which is in parallel with the arrangement direction of image capturing elements allows the strip pattern to be projected in parallel with the long side of solder coating area 5 as is illustrated in FIG. 7(*b*), thereby limiting the number of strips projected onto coated area 5. In contrast, the perpendicular arrangement of the long side of coated area 5 to the arrangement direction of image capturing elements increases the number of stripes projected onto coated area 5.

On the other hand, the use of a slit mask pattern having a 45 degree inclination to the arrangement direction 110 of image capturing elements as illustrated in FIG. 5(a), results in the strip pattern being projected onto coating area 5 at an angle as is illustrated in FIG. 7(a). A good number of strips are thus obtained regardless of whether the long side of coating area 5 is in parallel with or vertical to the arrangement direction of image capturing elements.

In either stripe pattern configuration of FIG. 7(a) or 7(b), the stripe pattern deviates at the border of the soldering cream coated area 5 in accordance with the height of the coating area. Therefore, the height of coated area 5 can be computed based on measurement of the amount of deviation of the stripe pattern.

Figure 8:
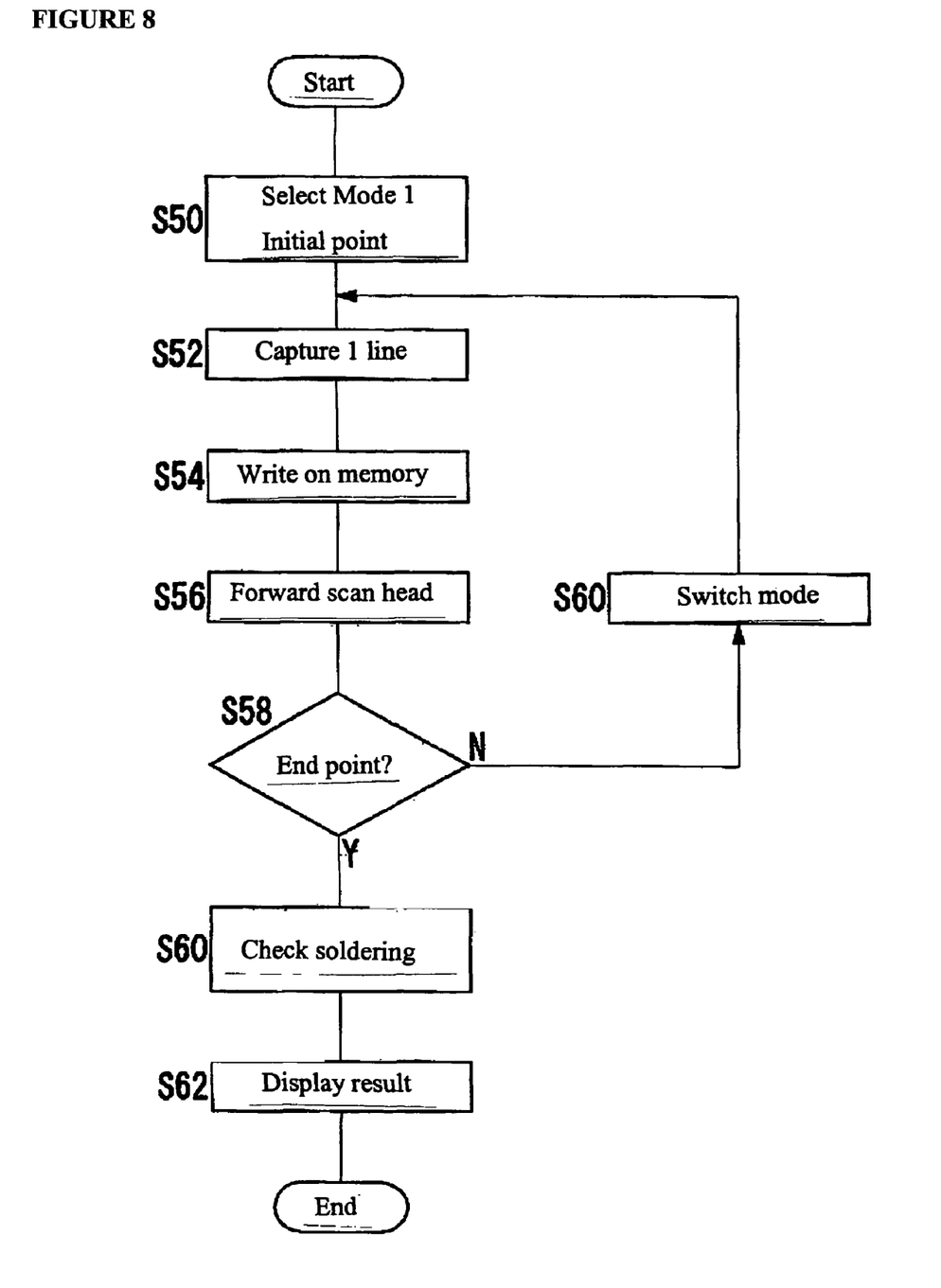
FIG. 8 is a flow chart illustrating the inspection procedure for the appearance inspection apparatus of Embodiment 1.

FIG. 8 is a flow chart illustrating the inspection procedure for this embodiment of the appearance inspection apparatus 10 of the present invention. Either side lighting or slit lighting is selected in accordance with a clock signal; an image for appearance inspection and another image for height measurement are formed at the same time while scanning head 16 moves one cycle on board 1. Here, the alternate scanning method represents the inspection procedure where odd lines including the first line, the initial position, are set up for appearance inspection; even lines are set up for height measurement.

First, an appearance inspection mode, hereinafter Mode 1, is selected and scanning head 16 is moved to the initial point (S50). Upon selection of the appearance mode, head control unit 40 lights up side light source 102 and turns off slit light source 103. Under the side light, light sensor 34 captures an image of the first line (S52) producing image data 54 which is written on memory 44 (S54).

Then, head control unit 40 moves scanning head 16 in the moving direction by one line (S56). The location of the scanning head 16 which should have been moved to the end of board 1, representing the end point of scanning, is checked with reference to the data associated with board 1 previously input (S58). If the scanning head 16 is not at the end point (N for S58), the mode is switched to the height measurement mode (S60). Upon selection of the height measurement mode, head control unit 40 turns off side light source 102 and turns on slit light source 103. Under the slit lighting, line sensor 34 captures the image of the second line, writes the image data 54 into memory 44, and moves scanning head 16 forward (S52, S54, and S56). The process steps are repeated until scanning head 16 reaches the end point such that odd line images are formed under the side lighting; the even line images are formed under the slit light.

When scanning head 16 reaches the end point, the process step is forwarded from Y for S58 to S60. In step S60, analysis unit 46 reads out from memory 44 the appearance inspection image data captured under the side lighting and corrects shading thereof based on the table that is set up for side light source 102 in correction value memory unit 49, thereby producing an appearance inspection image. Analysis unit 46 further checks pass or failure status of the soldering cream coated area for inspection points based on the appearance inspection image. Then, analysis unit 46 reads from memory 44 the height measurement image data captured under the slit light and corrects shading thereof based on the table that is set up for slit light source 103 in correction value memory unit 49, thereby producing a height measurement image. Analysis unit 46 further measures the height of the area defined by the soldering cream coating based on the height measurement image. In other words, accuracy of the soldering cream coating points is checked for each inspection point before the volume of the soldering cream is calculated from the height and area of the soldering cream coating. Validity of the amount of coating is thus tested. The pass or failure evaluation standard data for solder coatings is read out from evaluation standard memory unit 48 for the use in evaluation. The result is displayed when the inspection is finished (S62), when the entire process sequence ends. Note that pass or failure being displayed may also be recorded in memory 44.

As described above, in the above embodiment of the appearance inspection apparatus 10 of the present invention, an appearance inspection image and a height measurement image on which a stripe pattern is projected are obtained in one scanning cycle by switching. The solder coated area is accurately calculated utilizing an appearance inspection image, and the height of the coated area is calculated by correlating the stripe pattern with the height measurement image.

Embodiment 2

A second embodiment of the present invention is hereafter described in connection with FIG. 1 and FIGS. 9–12 respectively. The lighting unit 30 of test unit 14 further comprises a vertical light source 100 as shown in FIG. 9 to capture an appearance inspection image under vertical light. Only the difference in configuration and operation of Embodiment 2 from that of Embodiment 1 is described below. Common elements share the same reference number for each embodiment.

Figure 10:
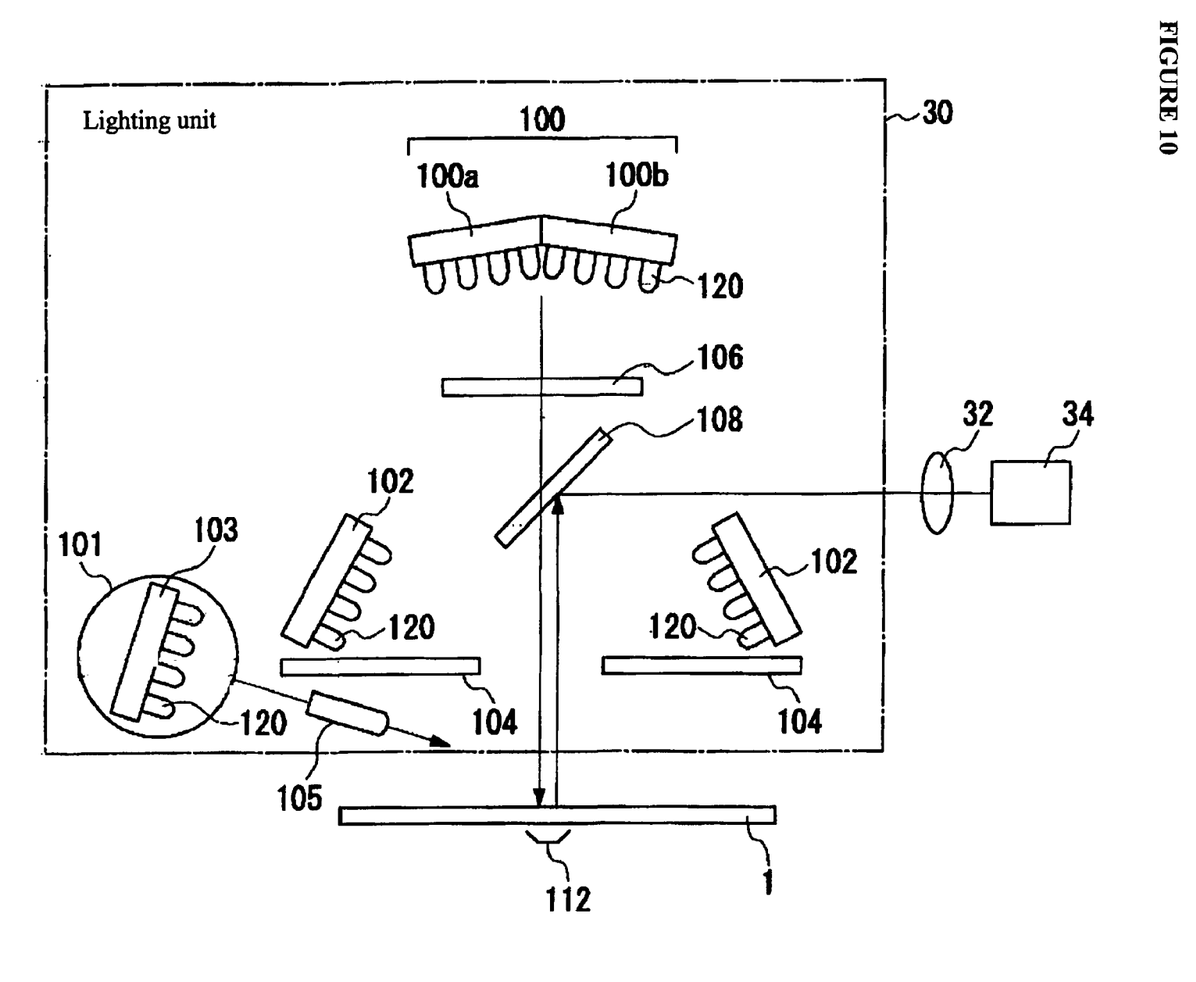
FIG. 10 is a diagram illustrating the test unit of FIG. 9.

FIG. 9 is a perspective view of the test unit 14 for Embodiment 2 of the inspection apparatus 10. FIG. 10 is a diagram illustrating the test unit 14 of FIG. 9 viewed from the initial point of scanning. In Embodiment 2 a lenticular sheet 106 is provided between vertical light source 1 and half mirror 108. The vertical light from vertical light source 100 passes through lenticular sheet 106, half mirror 108 and is projected onto the inspection surface of board 1 at an incident angle of "0". Lenticular sheet 106 takes advantage of deflection to set the component of light in a plane perpendicular to board 1 viewed from the image capturing direction.

As illustrated in FIG. 10, vertical light source 100 branches at the center thereof to provide sub-boards 100a and 100b, each having a group of LEDs 120 in the arrangement direction of image capturing elements of line sensor 34. These sub-boards 100a and 100b are formed in such a manner that they somewhat face each other to allow LEDs 120 to effectively project vertical light onto line 112 under inspection. Lenticular sheet 106 diffuses vertical light.

Lighting unit 30 lights up line by line utilizing the vertical light, the side light, and the slit light in the selected order by switching them. One cycle movement of scanning head 16 on board 1 produces: (1) appearance inspection image data from the vertical light; (2) appearance inspection image data from the side light; (3) and height measurement image data of the slit light at the same time. Referring to FIG. 1 for the purpose of comparing the embodiments, the correction value memory unit 49 for Embodiment 2 further comprises a table recorded with digital correction values obtained under the vertical light. Analysis unit 46 corrects shading of the appearance inspection image data with reference to a vertical lighting table to obtain the appearance inspection image data of vertical light. In this case, correction value memory unit 49 has a table recorded with correction values for all three types of lighting. Highly accurate images are thus obtained.

Figure 11:
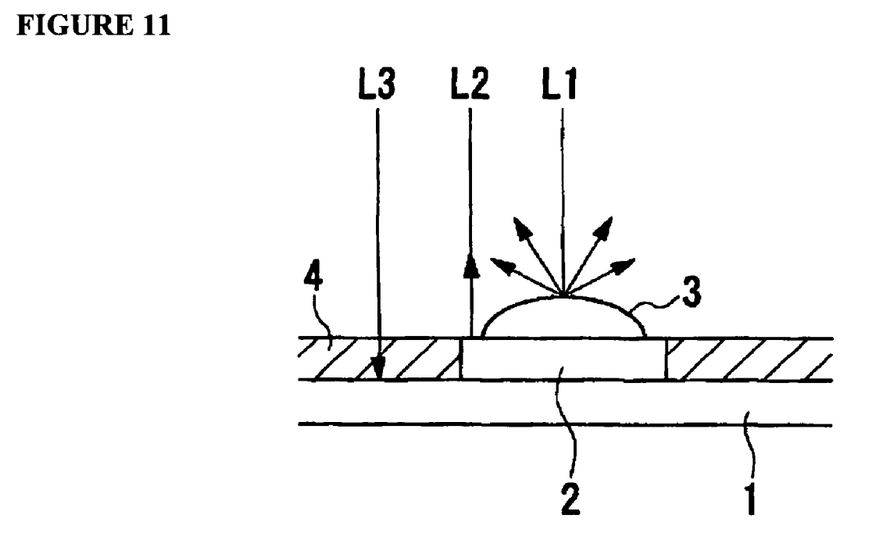
FIG. 11 is a cross section of the board on which soldering cream is coated.

FIG. 11 is a cross sectional image of board 1 upon which the soldering cream 3 is coated. Electrode 2 is coated with soldering cream 3. Components other than electrode 2 on board 1 are coated with a semitransparent solder resist film 4. The vertical light is irradiated onto board 1 from a point immediately above to capture the image thereof by line sensor 34.

Soldering cream 3 is a collection of fine spherical solder particles and their surfaces are rough with peaks and valleys. Light L1 irradiated onto these particles are scattered before light enters line sensor 34 via lens 32. As a result, the image of soldering cream 3 is captured in light gray. Electrode 2 is made of a metallic material such as copper foil having a mirror surface. Light L2 irradiated onto electrode 2 is thus reflected vertically, when it fully enters line sensor 34. The image of electrode 2 is, therefore, captured in bright white. Although light L3 irradiated onto semitransparent solder resist film 4 is transmitted to board 1, L3 is absorbed into the surface of board 1, which is in a dark color (e.g. dark green) resulting in an image for board 1 captured in black.

Figure 12:
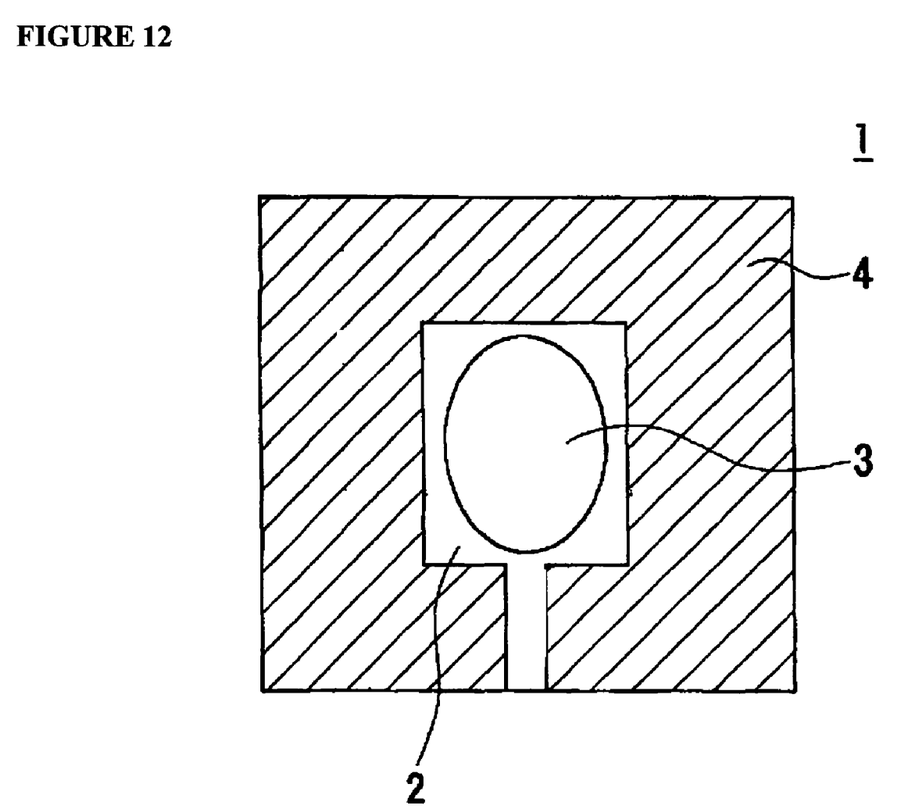
FIG. 12 is an image of a board having soldering cream coatings captured under vertical light.

FIG. 12 is a diagram illustrating the image of board 1 having soldering cream coatings, which is captured under the vertical light. The image of electrode 2 of board 1 is captured in white and that of the area covered by solder resist film 4 is captured in black, making clear detection of positions of electrodes 2 possible. The fact that the image of electrode 2 is captured in white while that of soldering cream 3 is capture in gray further provides a clear contrast at the border between soldering cream 3 and electrode 2, which makes the shape of the soldering cream 3 conspicuous.

As described above, an image capturing utilizing catoptrical light under vertical light allows discrimination of a mirror surface. Therefore, even though color data is limiting discrimination of electrode 2 from soldering cream 3, the use of a vertical light image allows accurate discrimination thereof. A combination of the appearance inspection image captured under the vertical light, the appearance inspection image captured by the side light, and the height measurement image captured by slit light allows accurate determination of validity of coating points of soldering cream 3 on electrode 2 and validity of the area of coating. The inspection accuracy is thus enhanced.

Embodiments of the present invention are described above. These embodiments are only examples. It is apparent for one of ordinary skills in the art to understand that many modifications are possible for each configuration element or data process, and these modifications will remain within the spirit of the present invention. Examples of these modifications are described below.

In the above second embodiment, moving scanning head 16 by one cycle on board 1, permits a height measurement image to be obtained, which better qualifies appearance inspection apparatus 10 for manufacturing lines. In this case, board 1 may be conveyed along a manufacturing line by fixing the scanning head 16 side and by providing a conveyer for the support base 22 such that board 1 can be inspected without being moved around.

Furthermore, in FIG. 1, although the test unit 14 and main unit 12 are integral components of the inspection apparatus 10, each may be located in a different place. For example, test unit 14 may be a part of a manufacturing line; main unit 12 maybe linked with an analysis center via any network. A business model may be established in such a manner that an analysis center having main unit 12 takes analysis orders from users having test unit 14.

The vertical light source of Embodiment 2 may be used in Embodiment 1 instead of a side light source to inspect the appearance inspection image captured under the vertical light and the height measurement image captured under the slit light.

REFERENCE SYMBOLS 1 board
3 soldering cream
10 appearance inspection apparatus
12 main unit
14 test unit
16 scanning head
30 lighting unit
32 lens
34 line sensor
40 head control unit
42 memory control unit
44 memory
46 analysis unit
48 evaluation standard memory unit
49 correction value memory unit
54 image data
100 vertical light source
102 side light source
104 acrylic sheet
106 lenticular sheet
108 half mirror
114 moving direction
120 LEDs

What is claimed is:

1. An appearance inspection apparatus for inspecting the appearance of a body comprising:

a scanning head for scanning the body to be inspected; and a main unit for controlling the inspection apparatus and said scanning head;

wherein said scanning head further comprises:

a lighting unit having multiple light sources for projecting light onto a surface of said body to be inspected at different given angles with respect to said body, said multiple light sources including a side light source, which projects light onto the surface of said body to be inspected at an angle and a slit light source, which projects a slit light at an angle; and a one-dimensional sensor comprising at least a plurality of arrays of multiple arrays of multiple image capturing elements for detecting light reflected from said surface of said body to produce image data; and wherein said main unit further comprises:

a head control unit for providing a control signal to said lighting unit for alternately switching between said side light source and said slit light source of said multiple lighting sources to create different lighting states from the light projected by each of said lighting sources respectively and for controlling the relative motion of said scanning head relative to said body;

a memory control unit for storing in memory image data corresponding to the projected light produced by said one-dimensional sensor from each lighting source respectively;

a correction value memory unit for storing multiple digital correction values in the form of a table for each lighting source and for the different lighting conditions for each lighting source; and an analysis unit for correcting shading resulting from said image data based upon selection of correction values stored in the correction value memory unit for each of the different lighting states switched by said head control unit to obtain an appearance inspection image of said body to be inspected.

2. The appearance inspection apparatus of claim 1 wherein said one-dimensional sensor comprises an array of multiple capturing elements corresponding to three (RGB) colors.

3. The appearance inspection apparatus of claim 2 wherein digital correction values are stored for each array of said RGB image capturing elements.

4. The appearance inspection apparatus of claim 2 wherein said multiple light sources of said lighting unit include:

a side light source, which projects light onto the surface of said body to be inspected at an angle; and a slit light source, which projects a slit light at an angle; and wherein said head control unit alternately switches said side light source and said slit light source for lighting said surface.

* * * * *